United States Patent [19]

Giacomoni et al.

[11] Patent Number: 5,776,241
[45] Date of Patent: Jul. 7, 1998

[54] PROCESS FOR THE PREPARATION OF A MELANIC PIGMENT OF SMALL PARTICLE SIZE AND ITS USE IN COSMETICS

[75] Inventors: Paolo Giacomoni, Enghien-les-Bains; Laurent Marrot, Livry-Gargan; Myriam Mellul, l'Hay-les-Roses; Annick Colette, L'Hay-les-Roses, all of France

[73] Assignee: L'Oreal, Paris, France

[21] Appl. No.: 815,662

[22] Filed: Mar. 10, 1997

Related U.S. Application Data

[63] Continuation of Ser. No. 360,844, filed as PCT/FR94/00467, Apr. 26, 1994, abandoned.

[30] Foreign Application Priority Data

Apr. 27, 1993 [FR] France ................... 93 04960

[51] Int. Cl.$^6$ ................... F08K 5/00
[52] U.S. Cl. ................... 106/498; 106/503; 8/127.5; 8/127.51; 8/127.6; 8/405; 8/425; 424/59; 424/60; 424/61; 424/701; 424/70.83; 424/401
[58] Field of Search ................... 106/498, 503; 8/127.5, 127.51, 127.6, 405, 425; 424/401, 59, 60, 61, 70.1, 78.03

[56] References Cited

U.S. PATENT DOCUMENTS

| | | | |
|---|---|---|---|
| 4,806,344 | 2/1989 | Gaskin | 424/59 |
| 4,806,360 | 2/1989 | Leong | 424/487 |
| 4,961,754 | 10/1990 | Grollier | 8/423 |
| 5,205,837 | 4/1993 | Anrean | 8/405 |
| 5,240,715 | 8/1993 | Ahene | 424/574 |
| 5,244,497 | 9/1993 | Junino | 106/498 |
| 5,380,359 | 1/1995 | Honda | 106/414 |
| 5,449,403 | 9/1995 | Andrean | 106/498 |
| 5,451,254 | 9/1995 | Andrean | 106/503 |
| 5,454,841 | 10/1995 | Wolfrum | 8/405 |

FOREIGN PATENT DOCUMENTS

| | | |
|---|---|---|
| 0441689 | 8/1991 | European Pat. Off. |
| 0518773 | 12/1992 | European Pat. Off. |
| 0524904 | 1/1993 | European Pat. Off. |
| 9001919 | 3/1990 | WIPO |

OTHER PUBLICATIONS

Koch et al., "Manufacture of color-stable C.I. Disperse Yellow 23", Chemical Abstracts, vol. 109, No. 4, Jul. 1988, Abstract No. 24238d; and DD-A-251 358.

Hirokazu, "Method for purifying melanin", Patent Abstracts of Japan, vol. 16, No. 485 (C-993) (5528), Oct. 1992 and JP-A-04-175-377.

Derwent Abstract 90-22600/30 (EP 379409) Grollier et al., Jul. 25, 1990.

*Primary Examiner*—Mark L. Bell
*Assistant Examiner*—Scott L. Hertzog
*Attorney, Agent, or Firm*—Cushman Darby & Cushman Intellectual Property Group of Pillsbury Madison & Sutro LLP

[57] ABSTRACT

Process for the preparation of a melanic pigment of small particle size and its use in cosmetics. The subject of the present invention is a process for the preparation of a melanic pigment of very small particle size in which 100% of the particles have a particle size smaller than 1µm, consisting in dissolving a melanin of natural and/or synthetic origin in an aqueous medium containing at least one alkalifying agent and/or at least one sequestering agent, and in precipitating the melanin thus dissolved by addition of at least one alkaline-earth metal salt. Another subject of the invention is the use of this pigment in compositions for cosmetic treatments and for dyeing hair.

15 Claims, No Drawings

PROCESS FOR THE PREPARATION OF A MELANIC PIGMENT OF SMALL PARTICLE SIZE AND ITS USE IN COSMETICS

This application is a continuation of Ser. No. 01360,844, filed as PCT/FR94/00467, Apr. 26, 1994, abandoned.

The invention relates to a process for the preparation of a new melanic pigment of small particle size, to its use in cosmetics and to a cosmetic composition containing it and to a process for colouring keratinous fibres (hair, fur) or the skin or for protecting the epidermis, making use of such a pigment.

Melanic pigments are pigments which are known in themselves. They are more particularly pigments which are responsible for the colouring of the hair, of the skin or of hair or fur of human or animal origin. They can also be prepared by synthesis, in particular by oxidation of indole derivatives such as more particularly 5,6-di-hydroxyindole.

Melanic pigments which have a small particle size are particularly advantageous insofar as they exhibit a good hiding power, and this allows them to be employed in lower concentrations in comparison with pigments which have a larger particle size, with a view to obtaining the same colour.

The advantage of the pigments which have a small particle size also lies in their cosmetic characteristics, especially where the feel is concerned. Compositions based on pigments of small particle size, in fact, feel softer.

The known melanic pigments have a particle size which is generally between 100 and 150 microns and must be ground, for example in a mortar, with a mill, by micronizing or by other milling techniques, in order to obtain particles which have a particle size of between 15 and 20 microns.

To obtain a smaller particle size it is also necessary to grind these pigments, and this is generally performed in aqueous media. However, following this grinding and even after the pigment has been dried, a reagglomeration of the various particles is observed.

Cosmetic compositions containing pigments presented in this manner frequently have characteristics that are not very cosmetic, insofar as the particles are relatively coarse and irregular. Because of the agglomeration, the compositions are not aesthetic and are frequently relatively unstable and not very hiding.

U.S. Pat. No. 4,806,344 and 5,006,331 describe a process for the preparation of melanic pigments and their use in solar compositions. This process consists first of all in dissolving melanin in triethanolamine and then precipitating it by oxidation in the presence of ferric chloride. However, the pigments thus obtained form agglomerates which must be reduced by means of ultrasound.

For some cosmetic uses a diameter of between 15 and 20 µm is excessive and the problem then arises of being capable of generating powders of smaller particle size without, however, resorting to additional stages of reduction of the melanic pigments obtained to the desired particle size.

The Applicant has just discovered a new process for the preparation of melanic pigments of very small particle size, such that 100% of the number of the particles obtained have a particle size smaller than 1 µm and such that a population of at least 60% of the number of all the particles has a particle size of between 0.5 to 1.5 times the number-average particle size of this particle population. The pigment obtained is stable with time and does not reagglomerate. According to this process the pigment can be precipitated directly on hair in order to colour it in mild conditions or else it may be incorporated, after freeze-drying, in cosmetic compositions. These compositions are particularly unctuous and smooth, with more intense and more hiding colours.

The first subject of the invention is therefore a process for the preparation of a melanic pigment whose particles have a particle size distribution as defined above, consisting in dissolving a melanin of natural or synthetic origin in an aqueous solution containing at least one alkalifying agent and/or containing at least one sequestering agent and in precipitating the melanin thus dissolved by the addition of salts of alkaline-earth metals.

A second subject of the invention is a melanic pigment like that obtained by the process which is also a subject of the invention, which has a particular particle size distribution.

A further subject of the invention is the use of this pigment for colouring hair or for the preparation of cosmetic compositions making use of such a pigment.

Another subject of the invention is a process for colouring keratinous fibres making use of such a pigment.

Finally, a further subject of the invention is a process for making-up keratinous matter, a process for protecting the human epidermis against the detrimental effects of UV radiation, making use of the compositions containing at least one dispersion of melanic pigment of small particle size as defined below.

Other subjects of the invention will appear on reading the description and the examples which follow.

The process for the preparation of the melanic pigment of very small particle size in accordance with the invention consists:

in dissolving a natural and/or synthetic melanin at a temperature of between 10°C. and 50°C. in an aqueous medium containing at least one alkalifying agent and/or at least one sequestering agent, then in precipitating the dissolved natural or synthetic melanin by the addition of at least one alkaline-earth metal salt.

The precipitate of melanic pigments of small particle size which is thus obtained can then be isolated by various methods, such as filtration or centrifuging. Thus isolated, the pigment is freeze-dried.

The particle size analysis of the melanic pigment thus obtained shows that the pigment is characterized by a particle size distribution such that 100% of the number of the particles have a particle size smaller than 1 µm. Furthermore the analysis also shows that a population of at least 60% of the number of all the particles thus prepared has a particle size of between at least 0.5 and not more than 1.5 times the number-average particle size of this population of particles.

Conventional alkalifying agents which are capable of bringing the pH to a value higher than 11 are employed. Sodium hydroxide and potassium hydroxide may be mentioned by way of example. These alkaline agents are preferably employed in concentrations varying between 0.5 mM and 2M.

The sequestering agents employed in accordance with the invention, also called chelating agents, are chosen from compounds which have the ability to combine with di- or trivalent ions such as calcium, magnesium, copper, lead, iron and chromium, to form complexes which are particularly stable. Among compounds of this type those preferably employed are ethylenediaminetetraacetic acid (E.D.T.A.), ethylene glycol tetraacetic acid (E.G.T.A.), diethylenetriaminopentaacetic acid, ethylenediaminetetramethylenephosphonic acid and their sodium salts, or else histidine or citrates. These sequestering agents are generally employed in concentrations varying between 0.1 mM and 3M.

When such sequestering agents are employed, the pH of the medium is either adjusted to a basic pH value with the above alkalifying agents or buffered with the aid of a buffer solution such as, for example, the trihydroxymethylaminomethane/hydrochloric acid mixture.

The alkaline-earth metal salts are chosen from magnesium, calcium, strontium, barium or radium salts. According to the invention, magnesium chloride and calcium chloride are particularly preferred. These alkaline-earth metal salts are generally employed accord- ing to the invention in concentrations varying between 0.5 mM and 1M.

In accordance with the invention, the melanic pigments employed as starting materials may be of natural or synthetic origin.

The synthetic pigments are in particular pigments resulting from the oxidative polymerization of an indolic compound corresponding to the formula:

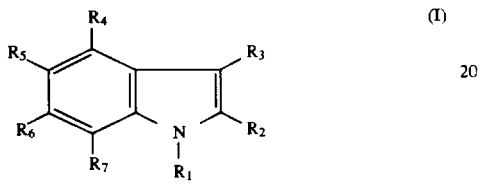

(I)

in which:

$R_1$ and $R_3$ denote, independently from one another, a hydrogen atom or a $C_1$–$C_4$ alkyl group, $R_2$ denotes a hydrogen atom, a $C_1$–$C_4$ alkyl group, a carboxyl group or a (C1–$C_4$ alkoxy)carbonyl group, $R_4$ and $R_7$ denote, independently of one another, a hydrogen atom, a hydroxyl, $C_1$–$C_4$ alkyl, amino or $C_1$–$C_4$alkoxy group, a ($C_2$–$C_4$ acyl)oxy group or a ($c_2$–$C_4$ acyl)amino group, $R_5$ denotes a hydrogen atom, a hydroxyl group, a $C_1$–$C_4$ alkoxy group, a $C_1$–$C_4$ alkyl group, a halogen atom, an amino group, a ($C_2$–$C_{14}$ acyl)oxy group, a ($C_2$–$C_4$ acyl)amino group, a trimethylsilyloxy group or a benzyloxy group, $R_6$ denotes a hydrogen atom, a hydroxyl group, a $C_1$–$C_4$ alkoxy group, an amino group, a ($C_2$–$C_{14}$ acyl)oxy group, a ($C_2$–$C_4$ acyl)amino group, a trimethylsilyloxy group, a ($C_2$–$C_4$ hydroxyalkyl)amino group or a benzyloxy group, it being also possible for $R_5$ and $R_6$ to form, jointly with the carbon atoms to which they are attached, a carbonyldioxy ring;

at least one of the radicals $R_4$ to $R_7$ denotes a group OZ or $NHR_8$, the radical Z of the group OZ denoting a hydrogen atom, a $C_2$–$C_{14}$ acyl group, a C1–$C_4$ alkyl group, a trimethylsilyl group or a benzyl group, the radical $R_8$ of the group NHR, denoting a hydrogen atom, a $C_2$–$C_4$ acyl or $C_2$–$C_4$ hydroxyalkyl group, not more than one of the radicals $R_4$ to $R_7$ denoting $NHR_8$, and not more than two of the radicals $R_4$ to $R_7$ denoting OZ, and, in the case where Z denotes a hydrogen atom, the two OH groups are in positions 5 and 6; and at least one of the radicals $R_4$ to $R_7$ denotes a hydrogen atom and, in the case where only one of these radicals $R_4$ to $R_7$ denotes a hydrogen atom while a single radical from $R_4$ to $R_7$ denotes $NHR_8$, or OZ, the other radicals denoting a $C_1$–$C_4$ alkyl group;

and their alkali or alkaline-earth metal, ammonium or amine salts.

The indolic compounds of formula (I) above are chosen from 4-hydroxyindole, 5-hydroxyindole, 6-hydroxy- indole, 7-hydroxyindole, 4-hydroxy-5-methoxyindole, 4-hydroxy-S-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl- 55,6-dihydroxyindole, 2-methyl-5,6-dihydroxyindol methyl-5,6-dihydroxyindole, 2,3-dimethyl-5,6-dihydroxyindole, 2-carboxy-5,6-dihydroxyindole, 20 4-hydroxy-5-methylindole, 2-carboxy-6-hydroxyindole, 6-hydroxy-N-methylindole, 2-ethoxycarbonyl-5,6-dihydroxy-indole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-25 6-hydroxy-2-ethoxycarbonylindole, 7-hydroxy-3-methyl-indole, 5-hydroxy-6-methoxy-2,3-dimethylindol 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5 indole, 6-N,β-hydroxyethylaminoindole, 4-aminoindole, 5-aminoindole, 6-aminoindole, 7-aminoindole, N-methyl-6-p-hydroxyethylaminoindole, β6-amino-2, 3-dimethylindole, 6-amino-2,3,4,5-tetramethylindole, 6-amino-2,3,4-tri-methylindole, 6-amino-2,3,5-trimethylindole, 6-amino-2,3,6-trimethylindole, 5,6-diacetoxyindole, 5-methoxy-6-acetoxyindole, 5,6-trimethylsilyloxyindole, the phosphoric ester of 5,6-dihydroxyindole, 5,6-dibenzyloxyindole and the addition salts of these compounds.

The indolic compounds which are particularly preferred are: 5,6-dihydroxyindole, 6-hydroxyindole, 7-hydroxyindole, 2-methyl-5,6-dihydroxyindolehydrobromide, 7-aminoindole, 3-methyl-5,6-dihydroxyindole, 4-hydroxy-5-methoxyindole and 2,3-dimethyl-5-methoxy-5 6-hydroxyindole.

The oxidative polymerization of the compounds of formula (I) can be performed in aqueous, water/solvent(s) or solvent(s) medium, in air, in the presence or absence of an alkaline agent and/o)r of an oxidizing agent such as hydrogen peroxide, preferably in the presence of an alkaline agent such as aqueous ammonia or in the presence of iodide ions, the iodide being preferably an alkali or alkaline-earth metal or ammonium iodide.

The oxidation of the compound of formula (I) can also be performed by employing periodic acid and its water-soluble salts and derivatives, permanganates and dichromates such as those of sodium or potassium, sodium hypochlorite, ammonium persulphate, sodium nitrite and organic oxidizing agents chosen from ortho- and para-benzoquinones, ortho- and para-benzoquinone mono- or diimines, 1,2- and 1,4-naphthoquinones, 1,2- and 1,4-naphthoquinone mono- or diimines, as described in application EP-A-0,376,776. The preferred salt of periodic acid is sodium periodate. The oxidizing agents can be activated by a pH modifier.

The preferred oxidative polymerization process makes use of hydrogen peroxide in the presence of aqueous ammonia. This oxidation reaction is generally performed at a temperature of the order of 20° C. to 100° C. and preferably 60° C. to 90° C.

It is also possible to undertake the formation of the starting synthetic melanic pigments in accordance with the invention by oxidation by an enzyme route. This oxidation is performed in an oxidizing medium in the presence of an enzyme with oxidative or peroxidative activity, such as the enzymes chosen from horseradish peroxidase, chloroperoxidase, milk peroxidase, cytochrome C-peroxidase, and products which have an activity similar to that of the peroxidative enzymes, such as haemoglobin.

methaemoglobin, myoglobin and metmyoglobin. This enzymatic oxidation can also be performed in the presence of tyrosinase with atmospheric oxygen. In particular, the indolic pigment may be obtained by polymerization of tyrosine in the presence of tyrosinase with atmospheric oxygen.

The implementation of the oxidative polymerization is preferably performed by introducing the indolic compound of formula (I) into an aqueous medium or into a mixture of water and of one or more solvents which may contain up to 95% of solvent or else into one or a number of anhydrous solvents, that is to say containing less than 1% of water.

Among the solvents that can be employed reference may be made to the $C_1$-$C_4$ lower alcohols such as ethyl alcohol, propyl or isopropyl alcohol, tert-butyl alcohol, alkylene glycols such as ethylene glycol, propylene glycol, alkylene glycol alkyl ethers such as ethylene glycol monomethyl, monoethyl or monobutyl ethers, propylene glycol and dipropylene glycol monomethyl ethers, and esters such as methyl lactate. The preferred solvent medium is a hydroalcoholic medium containing from 1 to 10% of ethyl alcohol.

In accordance with the processes the oxidizing agent and the indolic compound of formula (I) are left in contact for a few minutes to a few days.

The alkalifying agents are preferably chosen from sodium hydroxide, alkali metal carbonates or aqueous ammonia, in proportions of between $5 \times 10^{-4}$% to 10% by weight relative to the weight of the composition subjected to the oxidation.

When an iodide is employed in the presence of hydrogen peroxide, sodium or potassium iodide is preferably employed in a concentration of between 1 and 6%.

The coloured pigment resulting from the oxidative polymerization is obtained in insoluble form. It is isolated by filtration or centrifuging. To remove the traces of unreacted compound of formula (I) the pigment may be washed with water before or after filtration or centrifuging.

In the case where an oxidative polymerization process is used in air, the pigment may also be isolated by freeze-drying.

A melanic pigment which has a particle size of 100–150 μm is thus obtained, which is then ground by a conventional route such as, for example, with a mortar grinder, by micronizing or other milling techniques, until its particle size is of the order of 15 to 20 μm.

Melanin which is, for example, extracted from keratinous fibres such as human hair or else squid melanin can be employed as natural melanin.

These melanic pigments are employed in the process of the invention in concentrations varying between 0.1 and 10 %.

After the process of the invention has been applied a melanic pigment is obtained which is characterized by a particle size distribution such that more than 100% of the number of the particles have a particle size smaller than 1 μm. In addition, a population of at least 60% of the number of all the particles has a particle size of between at least 0.5 and not more than 1.5 times the number-average particle size of this particle population. These melanic pigments also form a subject of the invention.

Another subject of the invention is the use of these melanic pigments of small particle size for the preparation of cosmetic compositions or for colouring hair.

The melanic pigment of very small particle size which is obtained according to the process of the invention can be employed, after freeze-drying, for the preparation of cosmetic compositions.

In these compositions the concentration of melanic pigments according to the invention is between 0.001 and 20 % by weight.

The dilution of the, melanic pigment of the invention does not modify its quality, in the sense that the particle size remains substantially constant without any reagglomeration and/or sedimentation taking place.

When the compositions are employed for making-up the skin, eyelashes and eyebrows, such as a skin treatment cream, foundation, lipstick, eye shadow, blusher, liner also known as "eye-liner", or mascara, they may be presented in anhydrous or aqueous solid or paste form, such as oil-in-water or water-in-oil emulsions or else as dispersions, more or less thickened lotions, sticks or powders.

When these compositions are employed for the make-up of nails they may be in aqueous or anhydrous form.

These compositions have the advantage of being particularly stable and of exhibiting good harmlessness.

When the compositions are employed for protecting the human epidermis against UV radiation, they form so-called "solar" compositions and are generally presented in the form of dispersions in solvents or fatty substances or else in the form of emulsions such as creams and milks, ointments, gels, solid sticks or aerosol foams. The emulsions may additionally contain surfaceactive agents which are well known in the state of the art, such as anionic, nonionic, cationic or amphoteric surface-active agents.

When the cosmetic composition according to the invention is employed for colouring hair, it may be in the form of shampoo, lotion, gel or rinsing composition, to be applied before or after shampooing, before, during or after permanent waving or straightening, styling or treating lotion or gel, lotion or gel for blow-drying or setting, hair lacquer, and composition for permanent waving or straightening or colouring the hair.

The make-up compositions and the solar compositions may also contain fatty substances, organic solvents, silicones, thickeners, softeners, sunscreens, foam-suppressors, hydrating agents, perfumes, stabilizers, antioxidants, fillers, sequestrants, treatment agents such as anionic, cationic, nonionic or amphoteric polymers or their mixtures, propellants and alkalifying or acidifying agents.

The fatty substances may consist of an oil or a wax or mixture thereof, fatty acids, fatty alcohols, vaseline, paraffin wax, lanoline, hydrogenated lanoline or acetylated lanoline.

The oils are chosen in particular from animal, vegetable, mineral or synthetic oils and especially hydrogenated palm oil, hydrogenated castor oil, vaseline oil, liquid paraffin and Purcellin oil.

The waxes are chosen especially from animal, fossil, vegetable, mineral or synthetic waxes, and reference may be made to beeswaxes, carnauba and candelilla waxes, sugar cane wax, Japan wax, ozokerites, montan wax, microcrystalline waxes, paraffins and silicone waxes.

The compositions in accordance with the invention may also contain, in addition to the melanic pigments, other pigments which are generally employed in cosmetics, especially pearly and/or pearlescent pigments which make it possible to vary the colours capable of being obtained or to increase protection against ultraviolet radiation. In this latter case, metallic pigments such as titanium, zinc, cerium or zirconium oxides are employed.

"Nanopigments" with a particle size smaller than 100 nm and preferably of between 5 and 50 nm are preferably employed. The nanopigments may be coated or uncoated.

Another subject of the invention is a process for colouring keratinous fibres and more particularly human hair, which consists in precipitating the melanic pigment of small particle size directly on the said fibres after the latter have been brought into contact with the dissolved melanin in an aqueous medium containing at least one alkalifying agent and/or at least one sequestering agent as defined above, by applying to these fibres a composition containing at least one alkaline-earth metal salt as defined above.

The following examples are intended to illustrate the invention without, however, being of a limiting nature.

EXAMPLES OF PREPARATION

Example 1

0.2 g of melanic pigment resulting from the oxidative polymerization of 5,6-dihydroxyindole is dissolved in 100 g of a 0.1N sodium hydroxide solution, with stirring at 37° C. for 24 hours. 0.95 g (0.1 mol) of magnesium chloride is added to this solution. The solution precipitates. The precipitate is recovered by centrifuging and is then freeze-dried. A black pigment is obtained in which 100% of the particles have a particle size smaller than 1 μm and in which the mean diameter of these particles is 350 nm. In addition, a population of 70% of these particles has a particle size included in a range centred on 160 nm.

Example 2

The procedure is the same as in Example 1 except that the magnesium chloride is replaced with 1.1 g (0.1 mol) of calcium chloride. A black pigment is obtained in which the particle size is between 500 and 900 nm.

Example 3

1 g of the pigment resulting from the oxidative polymerization of 5,6-dihydroxyindole is dissolved in 100 ml of 1N sodium hydroxide with stirring for 2 days at 45° C. 0.95 g of magnesium chloride (0.1 mol) is added to this solution. The solution precipitates. After centrifuging and freeze-drying a black pigment is obtained in which 100% of the particles have a particle size smaller than 400 nm, and in which the mean particle diameter is approximately 220 nm.

In addition, 60% of the number of these particles have a particle size included in a range varying between 200 and 370 nm and have a number-average particle size of 250 nm.

Example 4

5 mg of synthetic melanin obtained by oxidative polymerization of tyrosine using ammonium persulphate are dissolved in 1 ml of a 0.1N histidine solution. After dialysis against a buffered trihydroxymethylaminomethane/ hydrochloric acid (10 mM) solution, the pH of which is 8, the melanin is dissolved in water in a proportion of 0.5 mg/ml.

The addition of 0.02 mg ($2 \times 10^{-3}$ mol) of magnesium chloride results in precipitation. After freeze-drying, 100% of particles are obtained in which the particle size is smaller than 800 nm and in which the mean particle diameter is 420 nm.

In addition, 66% of the particles have a particle size included in a range centred on 230 nm.

Example 5

Melanin from red hair is extracted by incubation of 100 mg of red hair for 3 hours in 1 ml of a sodium hydroxide solution (50 mM) at a temperature of 70° C. The supernatant is recovered by centrifuging and its pH is adjusted to 9 with hydrochloric acid. After purification by incubation overnight with 1 mg/ml of proteinase, the supernatant is precipitated by addition of 1N hydro.-chloric acid, centrifuged, washed with dilute hydrochloric acid (5 mM) and is then freeze-dried. The freezedried product is next dissolved in a buffered trihydroxymethylaminomethane/hydrochloric acid (10 mM) solution, the pH of which is 8. The solution obtained is next precipitated by adding 0.01 mg ($1 \times 10^{-3}$ mol) of magnesium chloride. 100% of particles are obtained, in which the particle size is smaller than 300 nm and in which the mean particle diameter is 140 nm.

In addition, 89% of the particles have a particle size included in a range centred on 80 nm.

EXAMPLES OF FORMULATION

Example 1: Colouring by precipitation on hair

A lock of bleached hair is soaked in 500 ml of a 10 mM EDTA solution containing 4 mg/ml of synthetic melanin obtained by oxidative polymerization of tyrosine using ammonium persulphate. The addition of 20 mmol (0.95 g) of magnesium chloride produces a light-chestnut colouring of this hair.

Example 2

A mascara of the following formula is prepared:

| | |
|---|---|
| stearic acid | 6.0 g |
| glyceryl stearate | 3.7 g |
| beeswax | 5.5 g |
| carnauba wax | 1.9 g |
| paraffin wax | 7.5 g |
| rosin | 1.83 g |
| propyl para-hydroxybenzoate | 0.05 g |
| pigment obtained in Example 1 | 0.8 g AS |
| methyl para-hydroxybenzoate | 0.23 g |
| hydroxyethyl cellulose | 0.22 g |
| triethanolamine | 3.0 g |
| acacia gum | 5.8 g |
| water q.s. | 100.0 g |

An unctuous and smooth black mascara is obtained which exhibits a fine dispersion of the pigment under an optical microscope.

Example 3

An eyeliner of the following formula is prepared:

| | |
|---|---|
| lauryl sorbitan oxyethylenated with 20 moles of ethylene oxide | 1.5 g |
| propylene glycol | 5.0 g |
| polyvinyl alcohol | 20.0 g |
| ultramarine | 20.0 g |
| pigment obtained in Example 1 | 5.0 g AS |
| ethyl alcohol | 5.0 g |
| stabilizer | 5.0 g |
| water q.s. | 100.0 g |

A liquid and smooth black mascara is obtained which exhibits a fine dispersion of the pigment under an optical microscope.

Example 4

A foundation of the following composition is prepared:

| A: | mixture of glyceryl stearate and of an ester of polyethylene glycol and stearic acid, sold under the name "Arlacel 165" by I.C.I. | 2.1 g |
|---|---|---|
|  | lauryl sorbitan oxyethylenated with 60 moles of ethylene oxide | 0.9 g |
|  | cetyl alcohol | 0.5 g |
|  | stearic acid | 1.5 g |
|  | hydrogenated polyisobutene | 22.0 g |
|  | propyl para-hydroxybenzoate | 0.2 g |
| B: | triethanolamine | 0.75 g |
| C: | titanium dioxide | 5.0 g |
|  | iron oxide | 2.0 g |
|  | pigment obtained in Example 1 | 0.2 g AS |
| D: | glycerine | 3.0 g |
|  | methyl para-hydroxybenzoate | 0.2 g |
|  | water q.s. | 100.0 g |
| E: | cyclic polydimethylsiloxane | 3.0 g |
|  | Carbopol 940 sold by Goodrich | 0.15 g |
|  | xanthan gum | 0.4 g |

Phase A is melted at a temperature of between 70 and 80° C. and phase B is then added. Phase C is then added to the mixture of A+B with stirring and until a homogeneous dispersion is obtained. Phase D is then added with stirring so as to form an emulsion. Phase E is incorporated last, with stirring and at a temperature of approximately 40° C.

A smooth and unctuous foundation is obtained, exhibiting a fine dispersion of the pigment under an optical microscope.

We claim:

1. A process for the preparation of a melanin pigment particle of less than 1 μm from a melanin pigment particle of more than 1 μm, comprising dissolving a melanin pigment particle of larger than 1 μm selected from the group consisting of a melanin of natural origin and a melanin of synthetic origin at a temperature of between 10° C. and 50° C. in an aqueous medium containing at least one component selected from the group consisting of an alkalizing agent and a sequestering agent, and then precipitating the melanin thus dissolved by the addition of at least one alkaline-earth metal salt, whereby a melanic pigment particle of less than 1 μm is formed.

2. The process according to claim 1 wherein the aqueous solution contains at least one alkalizing agent capable of adjusting the pH to a value higher than 11.

3. The process according to claim 1, wherein the sequestering agent is selected from the group consisting of ethylenediaminetetraacetic acid, ethylene glycol tetraacetic acid, diethylenetriaminopepentaacetic acid, ethylenediaminetetramethylenephosphonic acid or their sodium salts, histidine and citrates.

4. The process according to claim 1, wherein the alkalizing agent is present in a concentration in the ranges of 0.5 mM and 2M.

5. The process according to claim 1, wherein the sequestering agent is present in a concentration in the range of 0.1 mM and 3M.

6. The process according to claim 1, wherein the salts of alkaline-earth metals are chosen from magnesium chloride and calcium chloride.

7. The process according to claim 1, wherein the salts of alkaline-earth metals are used in concentrations in the range of 0.5 mM and 1M.

8. The process according to claim 1, wherein the synthetic melanin results from the oxidative polymerization of an indolic compound corresponding to the formula:

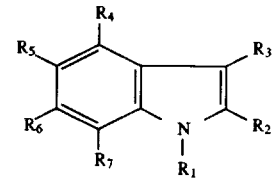

in which:

$R_1$ and $R_3$ denote, independently from one another, a hydrogen atom or a $C_1-C_4$ alkyl group, $R_2$ denotes a hydrogen atom, a $C_1-C_4$ alkyl group, a carboxyl group or a $(C_1-C_4$ alkoxy)carbonyl group, $R_4$ and $R_7$ denote, independently of one another, a hydrogen atom, a hydroxyl group, a $C_1-C_4$ alkyl group, an amino group or a $C_1-C_4$ alkoxy group, a $(C_2-C_4$ acyl)oxy group or a $(C_2-C_4$ acyl)amino group, $R_5$ denotes a hydrogen atom, a hydroxyl group, a $C_1-C_4$ alkoxy group, a $C_1-C_4$ alkyl group, a halogen atom, an amino group, a $(C_2-C_{14}$ acyl)oxy group, a $(C_2-C_4$ acyl)amino group, a trimethylsilyloxy group or a benzyloxy group, R6 denotes a hydrogen atom, a hydroxyl group, a $C_1-C_4$ alkoxy group, an amino group, a $(C_2-C_{14}$ acyl)oxy group, a $(C_2-C_4$ acyl)amino group, a trimethylsilyloxy group, a $(C_2-C_4$ hydroxyalkyl)amino group or a benzyloxy group, it being also possible for $R_5$ and RA to form, jointly with the carbon atoms to which they are attached, a carbonyldioxy ring;

at least one of the radicals $R_4$ to $R_7$ denotes a group OZ or $NHR_8$, the radical Z of the group OZ denoting a hydrogen atom, a $C_2-C_{14}$ acyl group, a $C_1-C_4$ alkyl group, a trimethylsilyl group or a benzyl group, the radical $R_8$ of the group $NHR_8$ denoting a hydrogen atom, a $C_2-C_4$ acyl or $C_2-C_4$ hydroxyalkyl group, not more than one of the radicals R4 to $R_7$ denoting $NHR_8$ and not more than two of the radicals $R_4$ to $R_8$ denoting OZ, and, in the case where Z denotes a hydrogen atom, the two OH groups are in positions 5 and 6; and at least one of the radicals $R_4$ to $R_7$ denotes a hydrogen atom and, in the case where only one of these radicals $R_4$ to $R_7$ denotes a hydrogen atom while a single radical from $R_4$ to $R_7$ denotes $NHR_8$ or OZ, the other radicals denoting a $C_1-C_4$ alkyl group;

and their alkali or alkaline-earth metal, ammonium or amine salts.

9. The process according to claim 1 wherein the natural melanin is extracted from keratinous fibres or from squid melanin.

10. The process according to claims 1 wherein the natural or synthetic melanin is employed in a concentration varying between 0.1 and 10% by weight of the total weight of the aqueous solution.

11. A cosmetic composition intended for making-up skin, eyelashes, eyebrows and nails, containing at least one melanic pigment of small particle size, obtained from the process as defined in claim 1.

12. A cosmetic composition intended for the protection of the human epidermis against UV radiation, containing at least one melanic pigment of small particle size, obtained from the process of claims 1.

13. A cosmetic composition according to claim 1 which contains from 0.001 to 20% by weight, relative to the total weight of the composition, of melanic pigment of small particle size.

14. A product consisting of particles of melanic pigment wherein a population of at least 60% of the number of all the particles has a particle size of between at least 0.5 and not more than 1.5 times the number-average particle size of this particle population.

15. A process for dyeing keratinous fibres comprising precipitating a melanic pigment of small particle size directly on said fibres by contacting said fibers with melanin dissolved in an aqueous medium containing at least one component selected from the group consisting of an alkalizing agent and a sequestering agent, and then applying to said fibers a composition containing at least one alkaline-earth metal salt selected from magnesium chloride and calcium chloride at a concentration in the range of between 0.5 mM and 1 M.

* * * * *